United States Patent [19]

Broido

[11] Patent Number: 4,833,913

[45] Date of Patent: May 30, 1989

[54] SAMPLE HAVING COATED PERFORATIONS INTENDED TO BE EXAMINED UNDER THE MICROSCOPE AND ITS PREPARATION PROCESS, PARTICULARLY FOR PRINTED CIRCUIT BOARDS

[75] Inventor: Georges H. G. Broido, Saint-Julien-en-Genevois, France

[73] Assignee: Hyprez S.A., France

[21] Appl. No.: 120,850

[22] Filed: Nov. 16, 1987

[30] Foreign Application Priority Data

Dec. 5, 1986 [FR] France ................ 86 17062

[51] Int. Cl.⁴ ............................................. G01B 21/08
[52] U.S. Cl. ................................................... 73/150 R
[58] Field of Search ........................ 29/464; 264/162; 428/13; 427/9, 10; 73/104, 865.8, 865.9, 432.1, 150 R

[56] References Cited

U.S. PATENT DOCUMENTS

| | | | |
|---|---|---|---|
| 2,494,834 | 1/1950 | Ringheim | 350/536 |
| 2,776,596 | 1/1957 | Eigen | 29/467 |
| 4,254,172 | 3/1981 | Takahashi et al. | 428/901 |

OTHER PUBLICATIONS

Preparation of Printed Circuit Microsections; Structure 10, Struers Nouveautés Metallographiques Apr. 1985.

Primary Examiner—Stewart J. Levy
Assistant Examiner—Robert R. Raevis
Attorney, Agent, or Firm—Steele, Gould & Fried

[57] ABSTRACT

Sample intended to be examined under the microscope which comprises a board having a perforation provided with a covering and embedded in resin. A checking device, of which the cylindrical rod has a diameter just less than that of the perforation, is inserted into the latter.

11 Claims, 2 Drawing Sheets

SAMPLE HAVING COATED PERFORATIONS INTENDED TO BE EXAMINED UNDER THE MICROSCOPE AND ITS PREPARATION PROCESS, PARTICULARLY FOR PRINTED CIRCUIT BOARDS

BACKGROUND OF THE INVENTION

The present invention relates to samples intended to be examined under the microscope, particularly samples of printed circuit boards or cards. These samples take the form of a board having coated perforations. The invention is also aimed at processes for preparing these samples.

The printed circuits, and more particularly the thickness of the metal covering of the wall of their perforations, are checked by examining, under the microscope, a section passing through the diameter of the perforation to be checked. It is essential, to that effect, that the plane of section passes exactly through the axis of the perforation. With regard to FIG. 4 of the journal "Structure 10, Struers Nouveautés Métallographiques" of April 1985, the very great precision required is demonstrated mathematically and it is proposed that it be achieved by means of a process of preparing samples which consists in piercing beforehand reference holes in the boards, in inserting therein two rods, in suspending the boards by the rods above a mould, in filling the mould with an embedding resin up to a level below the rods, in letting the resin which is used to support the board cure and put it under the microscope, in removing the embedded sample from the mould, in removing the rods and in prepolishing, that is, in abrading, then in polishing the sample as far as the perforations.

The success of this process necessitates great precision of location and diameter of the reference holes, which have no other use, and a special flask mould forming a reference level. The positioning rods must have very low tolerances so that the samples are supported properly in the mould. They are so difficult to remove after embedding that it has been necessary to design, to that effect, special equipment called a "rod extractor". However, in addition to these difficulties of implementation, the process suffers from a serious defect: the operator has no way at all of being aware that the operations have taken place correctly. It is necessary to put blind faith at one and the same time in his ability and in the equipment. He may thus discard good boards simply because the preparation of the sample is not correct or, more rarely, believe that the boards are good when they are faulty, but that the plane of the section is at fault.

The invention offsets these disadvantages by means of a sample prepared by a simpler process, which is quicker and yet more reliable than the previous process. Above all, the operator can see immediately with the naked eye that a sample has not been prepared correctly and more particularly that the section which ought to be subjected to inspection under the microscope is faulty.

OBJECTS AND SUMMARY

The invention therefore has as its object a sample which is intended to be examined under the microscope and which comprises a board having a perforation having a covering and embodded in resin. According to the invention a checking device is also embedded in the resin portion and the rod of the checking device of a diameter just less than that of the perforation is inserted therein.

Looking at the section, the operator sees immediately whether the rod is present along the whole axial length of the perforation. If this is not the case, the plane of the section is not perpendicular to the axis of symmetry of the sample. An error has been made. It is necessary to prepare a new sample.

According to an important development the checking device has a cylindrical head of greater diameter than that of the rod and of the same longitudinal axis as the latter. This time, the operator sees in the section not only the rod, but also the section of the head. If the section is trapezoidal, instead of being rectangular, the sample has not been prepared correctly for the same reason as above. If the width, that is the dimension which is perpendicular to the axis of the rod, of the section of the head is less than the original diameter of the head, the plane of section is parallel to that which it should be. It is necessary to prepare another sample.

In the most preferred embodiment of the invention, the checking device has a head, of which at least the end piece remote from the rod is conical. Checking no longer necessitates a comparison of the dimensions of the section of the head, but simply of its shape. The plane of section is not the right one if the angle at the summit of the cone does not appear there.

The lost checking device, permanently embedded and abraded at the same time as the sample, thus allows the operations to be checked.

In order to complete this check, it is recommended that two checking devices be inserted into two neighbouring perforations, preferably so that their heads are on the same side of the board. The sections of the two heads must have the same dimension and/or the two summits of the cones must appear. If this is not the case, the plane of section is not perpendicular to the axis of symmetry. It is necessary to prepare another sample.

The invention also has as its object a process which consists in putting the card into a mould having an axis of symmetry so that the axis of perforation is horizontal, in filling the mould with an embedding resin, in curing the resin in order to obtain an embedded sample and in abrading the embedded sample as far as the plane perpendicular to the axis of symmetry passing through a diameter of the perforation, characterised in that it consists, before putting the board into the mould, in inserting permanently into the perforation the rod of a checking device, which has a diameter just less than the diameter of the perforation, the checking device including a head of the same axis as the rod and of a diameter greater than the latter.

By inserting two checking devices in opposite directions into two perforations, it is certain that the plate is supported horizontally on the bottom of the mould by the two heads of the checking devices of the same diameter.

By inserting two checking devices in the same direction, every possibility that an erroneous plane of section be considered as right is excluded.

The checking devices are advantageously made of brass or of mass dyed aluminium with different colourings according to the diameters of the rods. The checking devices adapted to different perforations are thus simpler to recognize.

It is possible to check several boards at one and the same time by putting them on the same checking devices.

Preferably, the embedding resin is a transparent resin, more particularly a methacrylic resin.

BRIEF DESCRIPTION OF THE DRAWINGS

In the attached drawing given solely by way of example.

DETAILED DESCRIPTION OF THE PREFERRED EMBODIMENTS

Figure 1:
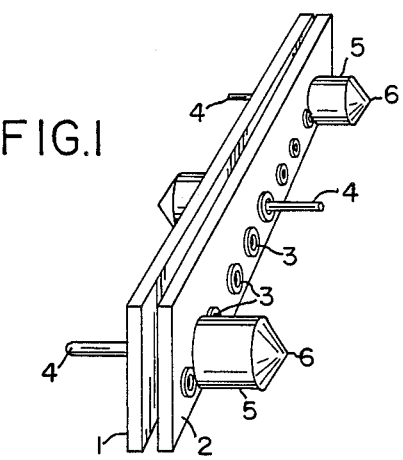
FIG. 1 is a perspective view illustrating the first stage of the process according to the invention.
Figure 2:
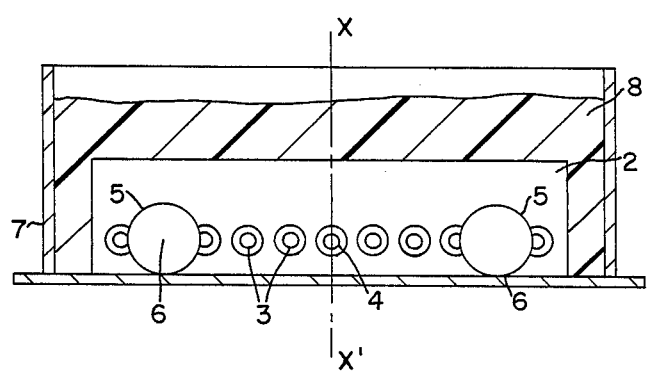
FIG. 2 is a view of the sample embedded in the mould, the front wall of the mould being removed.

In FIG. 1, the boards 1 and 2 are checked at the same time. Each card comprises eleven perforations 3, the interior walls of which are covered by a metal covering. The checking devices are inserted into three perforations 3. Each checking device is made up of a rod 4 of a diameter just less than that which a perforation 3 should have, covered once with a correct thickness of metal covering. The rod is extended by a head comprising a cylindrical portion 5 of a diameter clearly greater than that of the perforation and ends in a conical portion 6. The checking devices are identical. As the radius of the cylindrical portions 5 is greater than the distance between the centre of the perforations and the edge of the card, the boards 1 and 2 are held in a perfectly vertical manner by means of the checking devices. If one of the checking devices is not able to penetrate a hole, the board must be discarded. If the play is too great between the rod 4 and the diameter of a perforation 3, to the extent that the board is able to incline in relation to the vertical, the board must be discarded.

The second stage of the process consists in putting the assembly realized in accordance with FIG. 1 on the bottom of a horizontal mould 7. The mould has an axis of symmetry X, X', more particularly an axis of rotation. The mould is filled with an embedding resin 8 which may or may not be transparent. The resin is cured in order to obtain an embedded sample. The sample is removed from the mould.

Figure 3:
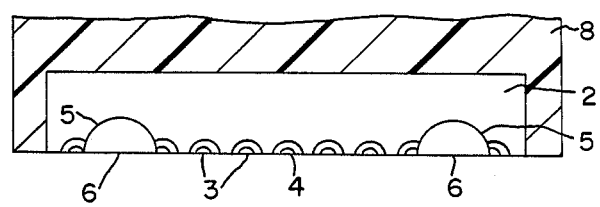
FIG. 3 is a view of the sample abraded as far as a plane passing through a diameter of the perforations.
Figure 4:
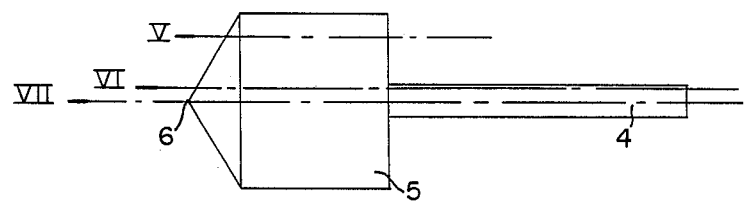
FIG. 4 is a view of a checking device on which three planes of section corresponding to FIGS. 5, 6 and 7 are shown.

The final stage of the process according to the invention consists in abrading the embedded sample as far as the plane perpendicular to the axis of symmetry X, X' passing through a diameter of the perforation. The sample represented in FIG. 3 which can be examined under the microscope is then obtained.

Figure 5:
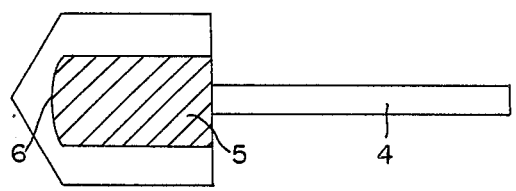
FIGS. 5, 6 and 7 are sectional views of the sample abraded along the various planes shown in FIG. 4.

In FIG. 5, the plane of the section is not the correct one. The rod will not appear in the perforation 3. The cylindrical portion 5 has dimensions which are much smaller than those which it should have. The cone 6 does not have a summit.

Figure 6:
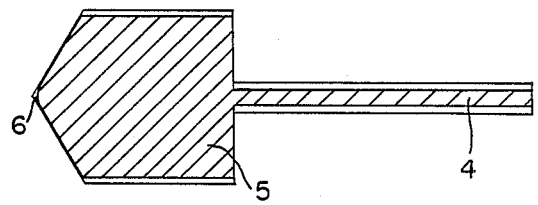

In FIG. 6, the plane of section is not correct either. The cylindrical portion 5 does not have the required dimensions. Above all, the summit of the cone 6 would not always appear.

Figure 7:
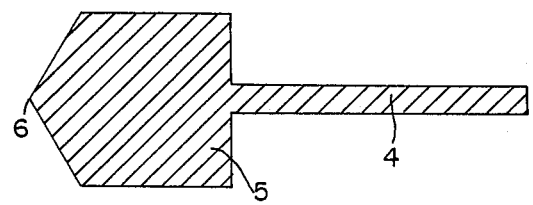

In FIG. 7, the plane of the section is good.

It is understood that if the plane of the section is faulty, whilst passing through the axis of one of the checking devices, it will not pass through the axis of a second checking device so that one of the checking devices will show that the plane is not the right one, or the rod will be truncated so that in that case too the plane is not the right one.

I claim:

1. Sample comprising a board, a coated perforation provided in the board, a resin material, in which the board is embedded, and a checking device which is also embedded in the resin material, the checking device includes a cylindrical rod which is inserted in the perforation, wherein the diameter of the rod is just less than that of the perforation.

2. The sample of claim 1, wherein the checking device has a cylindrical head with a diameter greater than that of the rod and the same longitudinal axis as the latter.

3. The sample of claim 1, wherein the checking device has a head, the head having an end portion, remote from the rod, which is conical.

4. The sample of claim 1, wherein the board comprises at least two perforations, and two checking devices are embedded in the resin material and inserted into said two perforations in such a way that the respective rods of the checking devices with a portion having a diameter greater than the diameter of the rod are on respective sides of the board.

5. The sample of claim 4, in which the checking devices have axes, wherein the sample is truncated along a plane defined by the axes of said two checking devices.

6. The sample of claim 1, in which the board comprises at least two perforations, and two checking devices are inserted into the two perforations so that the rods of the checking devices with a portion having a diameter greater than the diameter of the rod are on the same side of the board.

7. The sample of claim 6, in which the checking devices have axes, wherein the sample is truncated along a plane defined by the axes of said two checking devices.

8. A sample as claimed in claim 1 wherein said cylindrical rod of the checking device includes a cylindrical head having a diameter greater than the diameter of said rod, said head being coaxial with said rod, and an end portion of said head, remote from said rod, is conical.

9. Process for preparing a sample comprising a board, a coated perforation provided in the board and having an axis of symmetry, a resin material in which the board is embedded, and a checking device which is also embedded in the resin material, the checking device includes a cylindrical rod inserted in the perforation and having a portion with a diameter greater than the diameter of the rod, wherein the diameter of the rod is just less than that of the perforation, said process comprising the successive following steps:

inserting permanently into the perforation the rod of the checking device, to obtain a board with the rod inserted in the perforation, putting the board with the rod inserted in the perforation into a mold having an axis of symmetry so that the perforation axis of symmetry is horizontal, filling the mold with the resin material, cutting the resin material to obtain an embedded sample, and abrading the embedded sample as far as a plane that both contains the perforation axis of symmetry and is perpendicular to the axis of symmetry of the mold.

10. The process of claim 9, which comprises inserting at least two checking devices in the same direction into at least two perforations.

11. The process of claim 9, which comprises inserting at least two checking devices in opposite directions into at least two perforations.

* * * * *